(12) United States Patent
Matlashewski et al.

(10) Patent No.: US 6,489,105 B1
(45) Date of Patent: Dec. 3, 2002

(54) SCREENING METHOD FOR DETERMINING INDIVIDUALS AT RISK OF DEVELOPING DISEASES ASSOCIATED WITH DIFFERENT POLYMORPHIC FORMS OF WILDTYPE P53

(75) Inventors: Greg J. Matlashewski, St-Lazare (CA); Lawrence Banks, Gallo (IT); Alan Storey, St. Neots (GB)

(73) Assignees: McGill University, Montreal (CA); Imperial Cancer Research Technology, London (GB); International Center for Genetic Engineering and Biotechnology, Trieste (IT)

( * ) Notice: Subject to any disclaimer, the term of this patent is extended or adjusted under 35 U.S.C. 154(b) by 0 days.

(21) Appl. No.: 09/516,911

(22) Filed: Mar. 1, 2000

Related U.S. Application Data

(63) Continuation-in-part of application No. PCT/CA98/00828, filed on Aug. 31, 1998.

(30) Foreign Application Priority Data

Sep. 2, 1997 (CA) .............................................. 2214461

(51) Int. Cl.[7] .............................. C12Q 1/68; C12P 19/34
(52) U.S. Cl. ................................ 435/6; 435/5; 435/7.1; 435/91.2; 436/63; 436/501
(58) Field of Search ............................. 435/6, 5, 69.1, 435/91.2, 7.1; 436/501, 63; 514/44; 536/22.1, 23.1, 24.1, 24.31

(56) References Cited

U.S. PATENT DOCUMENTS 5,527,676 A 6/1996 Bert et al.

FOREIGN PATENT DOCUMENTS

| | | |
|---|---|---|
| EP | 0 518 650 | 12/1992 |
| EP | 0 710 722 | 5/1996 |
| WO | WO 92 13970 | 8/1992 |

OTHER PUBLICATIONS

Carcinogenesis, vol. 20, No. 9, pp. 1733–1736, 1999.*
Scheffner et al., 1990, Cell 63:1129–36.
Matlashewski et al., 1987, Mol. Cell. Biol. 7:961–963.
Storey et al., 1986, In the Keratinocyte Handbook by Irene Leigh et al., Cambridge University Press, 1994, p439–457.
Zhang et al., 1992, Gene 117:271–5.
Birgander et al., 1995, Carcinogensis 16:2233–2236.
Weston et al., 1994, Carcinogensis 15:583–587.
Weston et al., 1992, Env. Health Pers., 98:61–67.
Beckman et al., 1994, Hu. Herad., 44:266–70.

* cited by examiner

*Primary Examiner*—Laurie Scheiner
(74) *Attorney, Agent, or Firm*—Klauber & Jackson

(57) ABSTRACT

The present invention relates to a screening method to identify individuals at risk of developing diseases associated with different polymorphic forms of wildtype p53; which comprises the steps of: a) obtaining a biological sample from said patients; and b) determining the presence of p53pro or p53arg wildtype alleles in said sample; wherein the allele pattern of patients selected from the group consisting of p53pro/p53pro, p53arg/p53arg and p53pro/p53arg are indicative of a risk factor for developing disease associated with different polymorphic forms of wildtype p53. Notably, individuals who are p53arg/arg are at greater risk of developing pathologies associated with human papillomavirus infections, including cervical cancer.

12 Claims, 4 Drawing Sheets

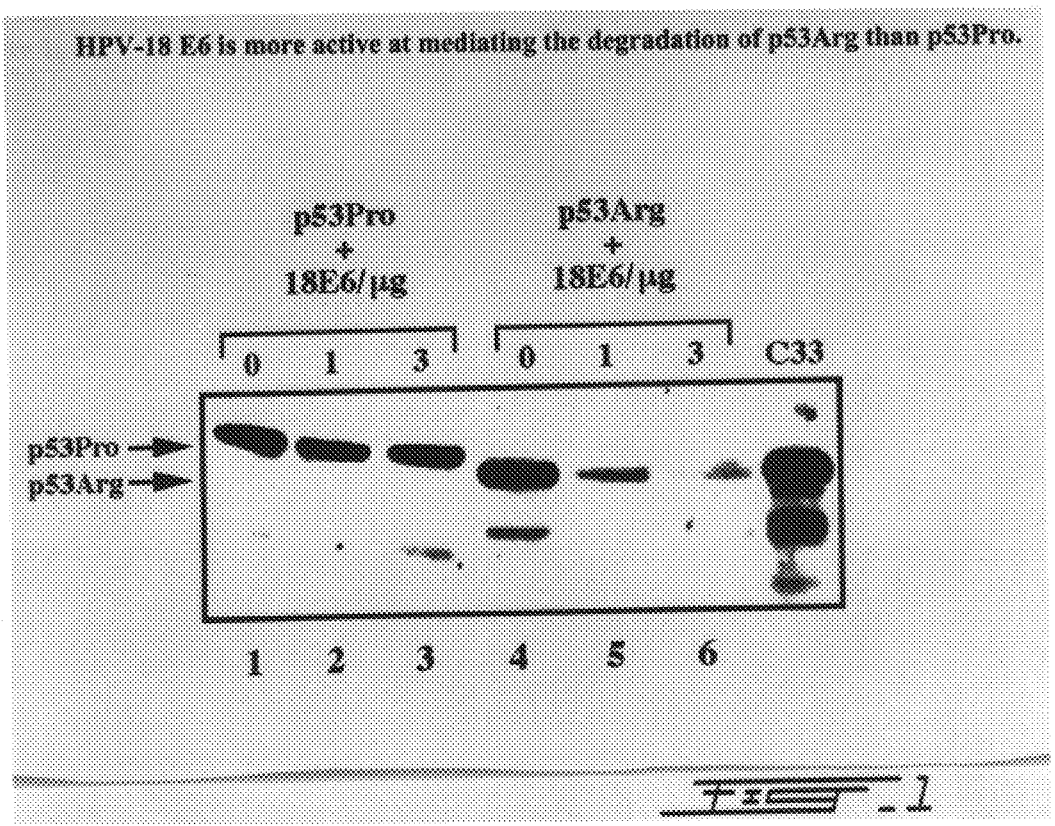

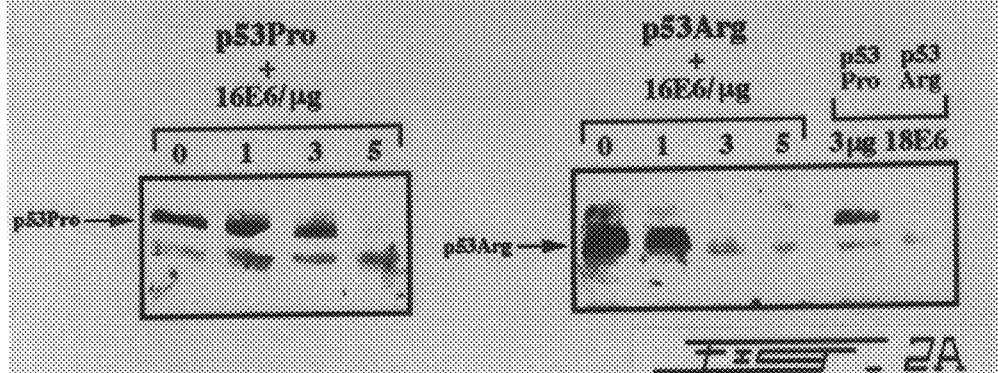
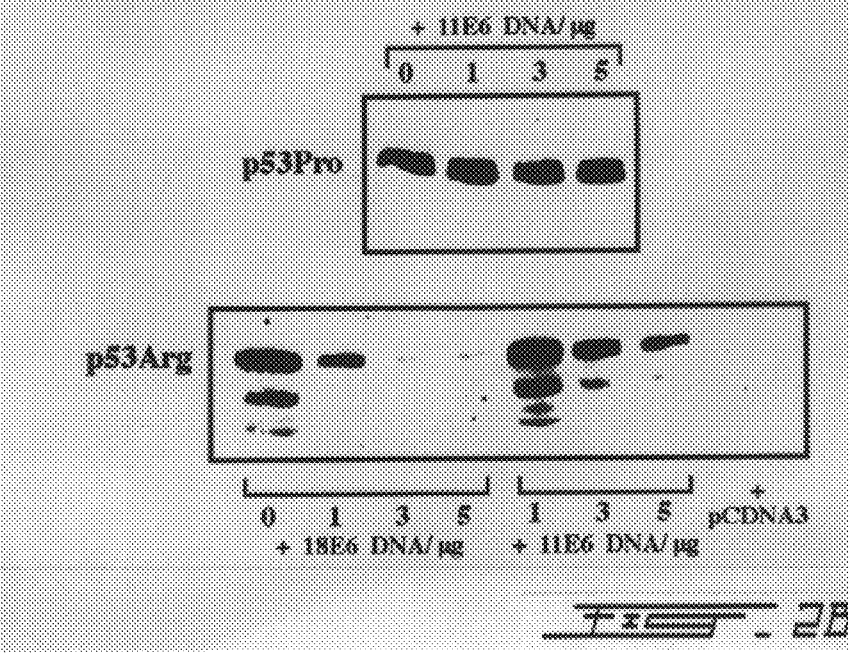

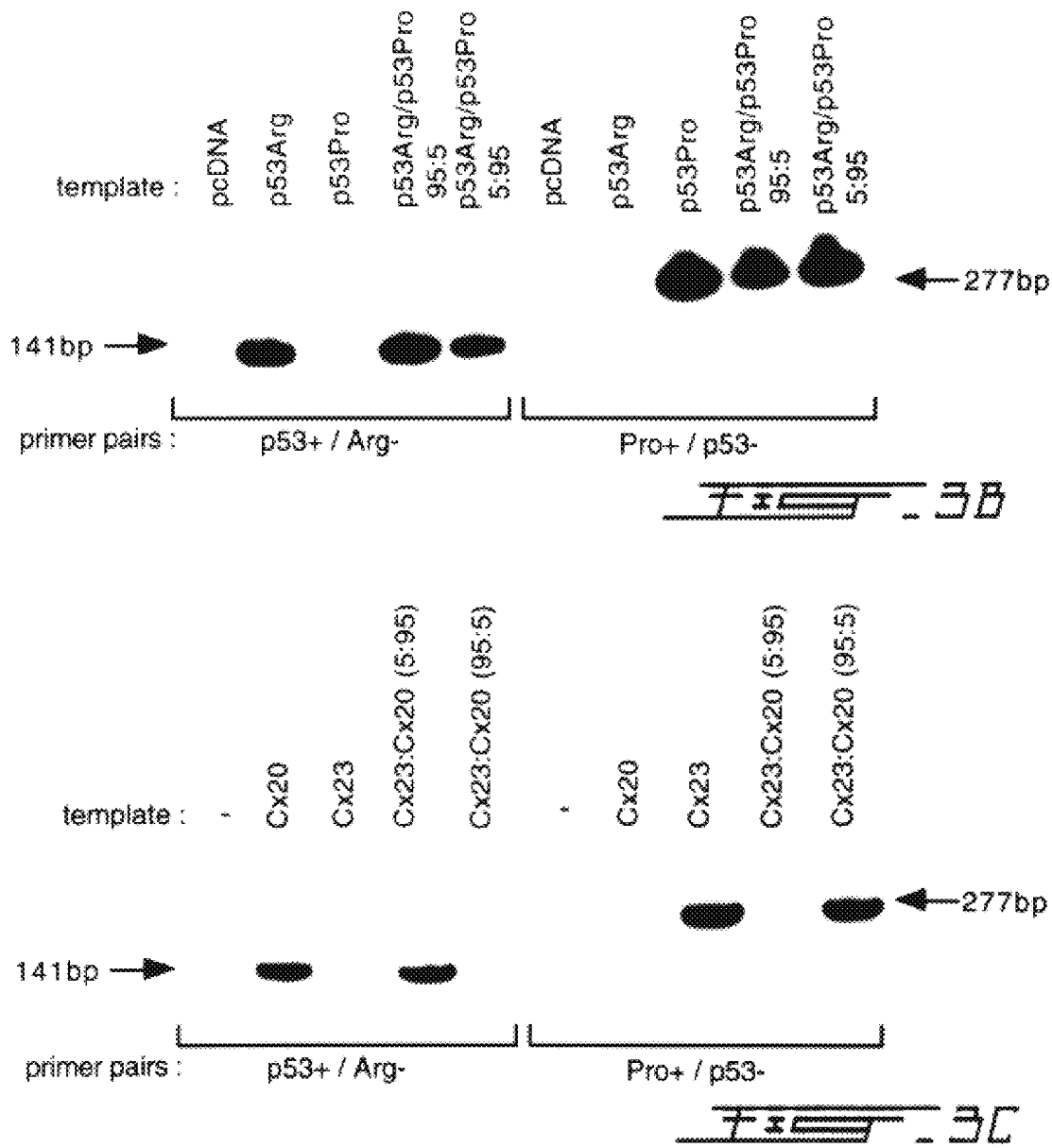

SEQUENCE LISTING

```
<160> NUMBER OF SEQ ID NOS: 4

<210> SEQ ID NO 1
<211> LENGTH: 18
<212> TYPE: DNA
<213> ORGANISM: Artificial Sequence
<220> FEATURE:
<223> OTHER INFORMATION: Human p53

<400> SEQUENCE: 1
gccagaggct gctccccc                                                 18

<210> SEQ ID NO 2
<211> LENGTH: 18
<212> TYPE: DNA
<213> ORGANISM: Artificial Sequence
<220> FEATURE:
<223> OTHER INFORMATION: Human p53

<400> SEQUENCE: 2
cgtgcaagtc acagactt                                                 18

<210> SEQ ID NO 3
<211> LENGTH: 18
<212> TYPE: DNA
<213> ORGANISM: Artificial Sequence
<220> FEATURE:
<223> OTHER INFORMATION: Human p53

<400> SEQUENCE: 3
tcccccttgc cgtcccaa                                                 18

<210> SEQ ID NO 4
<211> LENGTH: 18
<212> TYPE: DNA
<213> ORGANISM: Artificial Sequence
```

-continued

```
<220> FEATURE:
<223> OTHER INFORMATION: Human p53

<400> SEQUENCE: 4
ctggtgcagg ggccacgc                                                  18
```

SCREENING METHOD FOR DETERMINING INDIVIDUALS AT RISK OF DEVELOPING DISEASES ASSOCIATED WITH DIFFERENT POLYMORPHIC FORMS OF WILDTYPE P53

RELATED APPLICATIONS

This application is a continuation-in-part of PCT/CA98/00828 filed Aug. 31, 1998, now at the national phase, and claiming priority on Canadian patent application serial No. 2,214,461 filed Sep. 2, 1997, now abandoned.

BACKGROUND OF THE INVENTION (a) Field of the Invention

The invention relates to a screening method of to identify individuals at risk of developing diseases associated with different polymorphic forms of wildtype p53.

(b) Description of Prior Art

The cellular tumor suppressor protein, p53, is one of the major regulators of cell proliferation. Depending upon the context of the stimulus, p53 will induce cell growth arrest or programmed cell death (apoptosis). As a consequence this prevents continued proliferation of cells which have acquired DNA mutations and this regulation represents one of the organism's key defenses against cancer. In many human tumors inactivation of p53 is one of the principal factors in the development of the tumor. In Human Papillomavirus (HPV) associated cancers, however, p53 is almost always wild type. This is due to the activity of the viral E6 protein which labels p53 for ubiquitin mediated degradation and thus overcomes normal p53 functions. For this reason, HPVs are a major carcinogen for the development of cervical cancer in women, one of the most common forms of cancer world wide.

Two polymorphic forms of p53 exist which can encode either proline or arginine residues at amino acid position 72 of the p53 protein. This polymorphism results in a change in the migration of the p53 protein in polyacrylamide gels but, to date, both forms of p53 appear to have indistinguishable levels of activity. Indeed, numerous epidemiological surveys have been performed over the last 6-7 years in order to determine whether either polymorphism represents a risk factor for the development of several human tumors. Until now, the evidence has been overwhelmingly in favor of the view that the presence of proline or arginine at amino acid position 72 is not a significant risk factor in the development of any particular cancer.

However, based on our recent observations, it would be highly desirable to be provided with a screening method of to identify individuals at risk of developing diseases associated with different polymorphic forms of wildtype p53.

SUMMARY OF THE INVENTION

One aim of the present invention is to provide a screening method to identify individuals at risk of developing diseases associated with different polymorphic forms of wildtype p53.

In accordance with the present invention there is provided a screening method to identify individuals at risk of developing wildtype p53 related diseases; which comprises the steps of:

a) obtaining a biological sample from said patients; and b) determining the presence of p53pro or p53arg wildtype alleles in said sample; wherein the allele pattern of patients selected from the group consisting of p53pro/p53pro, p53arg/p53arg, p53pro/p53arg are indicative of a risk factor for developing disease.

The diseases may be selected from the group consisting of neoplasia, cancers, viral infections and viral pathologies which may (or may not) be caused by a virus.

Such viruses include, without limitation, human papillomaviruses, hepatitis B, adenoviruses or any other viruses which infect humans.

More particularly, the diseases include, without limitation, cervical warts, cervical neoplasia or cervical cancer.

For example, when a patient allele pattern is p53arg/p53arg it is indicative of an individual at greater risk of developing diseases including cervical warts, cervical neoplasia or cervical cancer which are associated with human papillomavirus (HPV) infections.

Viral pathologies also include skin cancer caused by human papillomaviruses, and including long term viral infections and susceptibility to initial viral infections in individuals who are p53arg/p53arg. More precisely, the determining of step b) of the present method consists in at least one of but not limited to:

a) amplifying by polymerase chain reaction;

b) sequencing DNA or protein;

c) hybridizing with at least one probe specific to either p53pro or p53arg DNA; and d) immunodetecting with at least one antibody specific to either p53pro or p53arg protein to identify the p53pro or p53arg alleles.

The screening method of the present invention may also be used to screen for patients which are under immunosuppressing therapy and are more susceptible for viral infections and viral pathologies.

In accordance with the present invention there is also provided a screening method for potential vaccination candidates in any HPV vaccination program, which comprises the steps of:

a) obtaining a biological sample from said patients;

b) determining the presence of p53pro or p53arg wildtype alleles in said; wherein p53arg/p53arg patients should be preferentially vaccinated.

In accordance with the methods of the present invention, the patients may have an abnormal PAP smear, low grade cervical lesions, may be newborns, or newborns to mothers with genital HPV infections.

For the purpose of the present invention the following terms and abbreviations are defined below.

"Diseases associated with different polymorphic forms of wildtype p53" is intended to mean any diseases involving p53 and wherein wildtype p53arg or p53pro behave differently. Such diseases include, without limitation, cancers caused by viruses such as papillomavirus.

"p53arg" is intended to mean p53arginine, wherein an arginine is found at amino acid position 72 of the p53 wildtype protein.

"p53pro" is intended to mean p53proline, wherein a proline is found at amino acid position 72 of the p53 wildtype protein.

"HPV" is intended to mean human papillomaviruses.

BRIEF DESCRIPTION OF THE DRAWINGS

FIG. 1 illustrates the comparison of HPV-18 E6 induced degradation of p53Pro and p53Arg in vivo;

FIGS. 2A and 2B illustrates HPV-16 and HPV-11 E6 preferentially target p53Arg over p53Pro for degradation in vivo;

FIG. 3B illustrates the detection of Arg and Pro p53 alleles from plasmid DNA; and FIG. 3C illustrates the amplification of p53 sequences from genomic DNA from Arg and Pro homozygous individuals.

DETAILED DESCRIPTION OF THE INVENTION

Figure 3A:
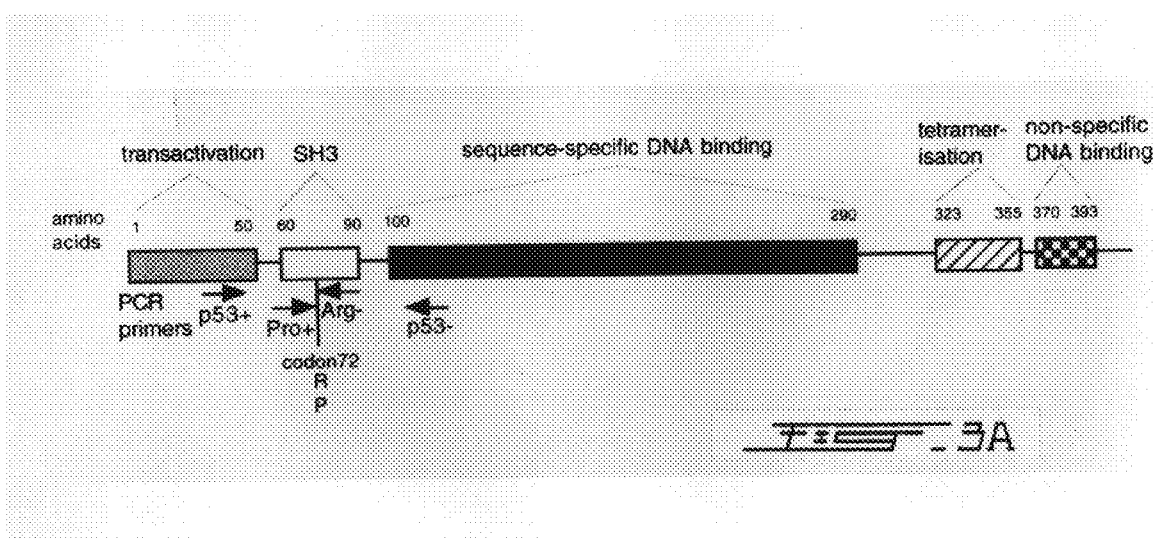
FIG. 3A illustrates the representation of the p53 gene showing functional domains of the protein.

In accordance with the present invention, we have been interested in determining whether the two forms of p53 are differentially targeted by the human Papillomavirus E6 proteins. We have shown that the arginine form of p53 is significantly more susceptible to E6 mediated degradation than the proline form of p53. This would argue that in a viral infection or in viral transformation, individuals expressing only arginine p53 would be more susceptible to the effects of the virus. A prediction from this would be that p53 arginine-only individuals would be more likely to develop HPV-associated tumors. In order to test this hypothesis, we have screened a series of patients with cervical cancer and also a series of renal transplant recipients (RTRs) with cutaneous cancer. After cervical cancer, cutaneous cancer represents the second major group of HPV-associated tumors. The results of this screen demonstrate an overwhelming preponderance of p53 arginine-only individuals in the cancer patients compared with a normal control population. This result demonstrates that p53 arginine-only individuals are much more likely to develop HPV-associated tumors than are heterozygous or p53 proline-only individuals.

The demonstration that different polymorphic forms of wildtype p53 are differentially susceptible to HPV inactivation is absolutely novel. The demonstration that p53 arginine-only individuals are more likely to develop HPV-associated cancers is also absolutely novel.

The E6 oncoprotein derived from tumor associated HPV types binds to, and induces the degradation of, the cellular tumor suppressor protein p53 (Scheffner, M. et al., 1990, Cell, 63:1129–1136). It has been shown that mutation of the p53 protein frequently renders it insusceptible to E6 mediated degradation, but there have been no comparable reports on the effects of E6 upon different polymorphic forms of wild type p53. In this study we have investigated the effect of the proline/arginine polymorphism at position 72 of the wildtype p53 protein (Matlashewski, G. et al. 1987, Mol. Cell. Biol., 7:961–963). The results demonstrate that, in vivo, p53Arg was significantly more susceptible to degradation by high risk derived HPV E6 than was p53Pro. Moreover, E6 from low risk HPV-11 could also mediate the degradation of p53Arg but not of p53Pro. Therefore, p53Arg is more susceptible to degradation by E6 proteins from both low risk and high risk HPV types than is p53Pro. Taken together, these results suggest that the proline/arginine polymorphism within wildtype p53 represents a susceptibility marker for HPV induced cancers.

It is well established that the development of cervical carcinoma correlates closely with the presence of certain Human Papillomavirus types, such as HPV-16 and HPV-18. In contrast, infection with other HPV types, such as HPV-6 and HPV-11, correlates mainly with the development of benign lesions (Storey A. et al., 1986, In the Keratinocyte Handbook by Irene Leigh et al., Cambridge University Press, 1994, p439–457). HPV-16 and HPV-18 encode two major oncoproteins, E6 and E7. The E7 protein binds to, and inactivates, the cellular tumor suppressor protein pRb; the E6 protein binds to the cellular tumor suppressor p53 and subsequently directs its degradation through the ubiquitin pathway. Although inactivation of these two tumor suppressor proteins by HPV is regarded as being important during tumor development, there are no clear indications as to whether there are other genetic factors which may predispose an infected individual to develop cervical carcinoma. The p53 protein is frequently mutated in a large number of human tumors but is invariably wild type in early cervical tumors, leading to the notion that inactivation of p53 by E6 is analogous to an inactivating mutation. Many of the mutant p53 proteins described in the literature are not susceptible to E6 mediated degradation, suggesting that the interaction between these two proteins can easily be disrupted. We have been interested in investigating whether polymorphisms within the wild type p53 protein can affect the ability of HPV E6 to label p53 for ubiquitin mediated degradation. we have focused our attention on the proline/arginine polymorphism at amino acid position 72 within the p53 protein, since this is not a conservative amino acid change and, indeed, the alteration results in a dramatic change in the migration of the p53 protein on SDS-PAGE (Matlashewski, G. et al. 1987, Mol. Cell. Biol., 7:961–963).

To investigate whether the HPV-18 E6 protein can preferentially recognize either of the two forms of p53 we first performed a series of in vivo degradation assays. p53 null Saos-2 cells were transfected with plasmids expressing one or other of the two polymorphic 35 forms of p53 together with increasing amounts of an HPV-18 E6 expressing plasmid. After 24 hrs the cells were extracted and the residual p53 protein detected by Western blot analysis with a pool of anti p53 monoclonal antibodies.

FIG. 1 shows a comparison of HPV-18 E6 induced degradation of p53Pro and p53Arg in vivo. In this experiment, Saos-2 cells were transfected with 3 ug of either pCDNA-p53Pro or pCDNA-p53Arg together with increasing amounts of pCDNA-18E6 or control plasmid pCDNA-3 as indicated. After 24 hrs the cells were extracted in a solution of 50mM Hepes pH 7.0, 250mM NaCl, 0.1% NP40 and 1% APROTININ™. Protein concentrations were determined using the Bio Rad protein assay and equal amounts were run on SDS-PAGE and transferred to a nitrocellulose membrane. p53 protein was detected using a pool of the anti p53 monoclonal antibodies pAb1801, 1802 and 1803 and the Western blot developed using the Amersham ECL system. Transfection efficiencies were monitored throughout by cotransfecting a lacZ expressing plasmid on parallel plates and staining for lacZ expression. C33 cells represent a positive control for p53 expression.

As shown in FIG. 1, it is clear that increasing amounts of HPV-18 E6 induces a dramatic decrease in the amount of p53Arg. In contrast, no significant degradation of the p53Pro was detected under identical conditions. These results show that the proline/arginine polymorphism at amino acid position 72 in p53 alters its susceptibility to HPV-18 E6 induced degradation in vivo and that p53arg is more susceptible to HPV-18 E6 than is p53.

We were next interested in determining whether this alteration in the susceptibility of p53 to E6 induced degradation was restricted to E6 derived from HPV-18 or whether it was also true for E6 proteins derived from other HPV types. To investigate this, we repeated the in vivo degradation assays performed in FIG. 1, including increasing amounts of HPV-16 E6 and HPV-11 E6. The results obtained are shown in FIG. 2.

Saos-2 cells were transfected with pCDNA-p53Pro or pCDNA-p53Arg, together with increasing amounts of pCDNA-16E6 (FIG. 2, Panel A) or pCDNA-11E6 (FIG. 2, Panel B) or control plasmid pCDNA-3 as indicated. Residual p53 protein was detected as in FIG. 1. pCDNA-18E6 was included for comparison.

The HPV-16 E6 protein (FIG. 2A) exhibits an ability to degrade the different forms of p53 which is similar to that seen with HPV-18 E6. As can be seen, only at high E6 input is any significant degradation of p53Pro obtained, whereas much lower concentrations of the HPV16 E6 protein produce complete degradation of p53Arg. Of particular interest however, are the results with the HPV-11 E6 protein (FIG. 2B). A number of in vitro studies had previously indicated that HPV-11 E6 could not target p53 for ubiquitin mediated degradation. The results with p53Pro in vivo would certainly support this view, since HPV-11 E6 was unable to mediate the degradation of p53Pro (FIG. 2B). However, HPV-11 E6 clearly induces the degradation of p53Arg in the in vivo assay, albeit not as efficiently as that induced by the oncogenic HPV-16 and HPV-18 E6 proteins. These results are extremely significant in that they demonstrate that the proline/arginine polymorphism within the p53 protein at position 72 determines the susceptibility of wildtype p53 to E6 mediated degradation, regardless of the type of HPV. In accordance with the present invention, we have shown a clear difference in the susceptibility of two polymorphic forms of wildtype p53 to E6 mediated degradation. Although both the HPV-16 and HPV-18 E6 proteins can induce the degradation of the proline form of p53, this degradation is much less efficient than that of the arginine form-of p53. Further, the HPV-11 E6 protein is completely inactive with respect to the p53Pro but nonetheless exhibits lower but significant levels of degradation on p53Arg. Since p53 represents a key control point in the host defense against tumor formation, these studies would predict that this polymorphism would have significant bearing on the likely outcome of an HPV infection. Several studies have addressed the p53 polymorphism within non HPV associated tumors and failed to show any significant correlation with the presence or absence of a particular polymorphic form of p53 (Zhang, W. et al., 1992, *Gene*, 117:271–275; Birgander R. et al., 1995, *Carcinogenesis*, 16: 2233–2236; Weston A. et al., 1994, *Carcinogenesis*, 15: 583–587; Weston A. et al., 1992, *Env. Health Pers.*, 98: 61–67). In contrast, our study strongly supports the hypothesis that in HPV associated tumorigenesis, the polymorphism within p53 at position 72 represents a significant risk factor. To test this hypothesis, we have examined the p53 genotype (p53pro or p53arg) in a series of HPV-associated cervical and skin cancers. The results of this screen for the p53 polymorphism in these HPV associated tumors confirms this hypothesis (see results in Tables 1 and 2). As detailed within, these data demonstrate that over 85% of individuals with HPV associated cervical cancer (Table 1) and skin cancer (Table 2) were homozygous for the p53arg allele. We can conclude that the nature of the p53 polymorphism at amino acid position 72 is a vital factor in HPV-associated tumorigenesis, and that individuals who are homozygous for p53arg are at greater risk of developing these tumors.

Method for Determining the Genotype of Wildtype p53 (p53pro or p53arg)

Tissue Samples

Tumor specimens included both invasive and cutaneous squamous cell. All lesions were histologically confirmed and were collected at the time of biopsy or surgical excision, snap-frozen and stored at −70C. Seven of the cervical SCCs were obtained from formalin-fixed, paraffin-embedded archival material. Samples for the control group was comprised of DNA extracted from whole blood collected from healthy volunteers.

DNA Extraction

DNA from frozen tissue was extracted by proteinase K digestion and phenol-chloroform extraction, DNA from paraffin-embedded tissue was similarly extracted after deparaffinization. DNA was extracted from whole blood from control individuals using a Nucleon DNA extraction kit (Scotlab).

PCR Amplification of p53 Polymorphic Sequences p53 Pro sequences were detected by PCR using the primer pair p53Pro+/p53−(p53Pro+: 5' GCCAGAGGCTGCTCCCCC (SEQ ID NO:1), p53−:5'CGTGCAAGTCACAGACTT (SEQ ID NO:2) and p53Arg by the primer pair p53+/Arg−(p53+: 5' TCCCCCTTGCCGTCCCAA (SEQ ID NO:3), Arg−: 5' CTGGTGCAGGGGCCACGC (SEQ ID NO:4)). Primer pairs (2 ug each) were mixed and end labeled with [32P] by polynucleotide kinase (Promega) in a total volume of 50 ul containing 50uCi [α32P] ATP (Amersham). 1 ul of the labeled primer mix was used per PCR reaction. PCR reactions (25 cycles) were performed in a total volume of 50 ul using 0.2 units of Red Hot polymerase (Advanced Biotechnologies) in reaction buffer IV (supplied by the manufacturer) at 1.5 mM Mg++. 10 ul of the reaction product was fractionated on a 8% polyacrylamide gel in 1×TBE buffer, dried and either exposed to X-ray film or quantitated using a Storm 840 phosphorimager (Molecular Dynamics) and ImageQuant software.

Results From p53 Genotyping

We first investigated the frequency of the p53 Pro and Arg alleles in a series of cervical cancer biopsies and compared this with the frequency observed in the control group (Table 1). The relative frequency of each is shown in parentheses.

TABLE 1

Frequency of detection of Arg and Pro alleles in normal volunteers and cervical tumor biopsies

|  | Pro | Arg | Pro/Arg |
| --- | --- | --- | --- |
| Normal N = 42 | 2 (0.05) | 15 (0.36) | 24 (0.57) |
| Cervical Cancers N = 24 | 2 (0.08) | 21 (0.88) | 1 (0.04) |

HPV types detected in cervical carcinomas: HPV16 N = 12, HPV18 N = 4, HPV45 N = 2, HPV positive but not typed = 6

Both groups comprised individuals of a broadly similar ethnic background, and the allelic frequencies we observed in our control DNA samples were similar to those observed in previously reported studies, given that p53 alleic frequency varies between different ethnic groups (Beckman, G. et al., 1994, Hu. *Hered.*, 44:266–270). In our study there was a marked difference in the frequency of the detection of the Arg allele relative to that of the Arg/Pro genotype, which was significantly different between the cervical cancer biopsies and the normal controls, ($x^2$=218.89, p=0.000013), with only the Arg allele being detected in a far greater number of samples (88% in the cancers versus 36% in the controls) with a concomitant reduction in the number of Pro/Arg genotypes observed (4% in the cancers compared with 57% in controls). There was no significant difference between the frequency of detection of only the Pro allele in this study, although the numbers in each group were small.

The clear distinction in the allelic frequencies between the cervical tumor samples compared with the control group, shows that the presence of the p53arg allele in the absence of the Pro allele confers a susceptibility to the development of the disease in cervical tumors harboring a high risk HPV type. This is in marked contrast to other tumors (Zhang, W. et al., 1992, Gene, 117:271–275; Birgander R. et al., 1995, Carcinogenesis, 16: 2233–2236; Weston A. et al., 1994, Carcinogenesis, 15: 583–587; Weston A. et al., 1992, Env. Health Pers., 98: 61–67) where no significant differences in p53 polymorphic frequencies have been observed between tumor and control biopsies. The fact that the p53Arg protein is more easily inactivated by being more susceptible to E6-mediated proteolytic degradation correlates strongly with the tumor p53 genotype findings.

In addition to their well documented role in cervical cancer, HPVs have been postulated to be involved in the development of cutaneous carcinomas. In immunosupptessed individuals such as renal transplant recipients, a broader spectrum of viral types are found in the lesions and unlike cervical tumors, these lesions often contain more than one HPV type. In addition to previously defined HPV types, several newly identified EV-related HPV sequences have also been identified in biopsies from RTRs. We then extended our p53 polymorphism studies to include tumors derived from renal transplant recipients, the results of which are shown in Table 2.

TABLE 2

| Patient code | SCC | HPV Type(s) | Arg/Pro Status of Tumor (R/P) |
|---|---|---|---|
| CW | 2H | 27 | R |
|  | 7S | 10 | R |
|  | 7U | 28 | RP |
| CR | 2L | HPVRTRx5* | R |
| AO | 3D | 3, 20, 23 | RP |
| DE | 3U | 10, HPVRTRx5* | R |
|  | 3V | HPVRTRx5* | R |
|  | 3X | HPVRTRx1* | R |
|  | 7L | 10, 23 | R |
|  | 7M | 5 | R |
|  | 7Q | 10, 23 | R |
| DL | 3Y | 1, 10 | R |
|  | 3Z | 1, 27 | R |
|  | 4A | 27 | R |
| BM | 4B | 27, 36 | R |
|  | 4E | 19, 27 |  |
|  | 7F | 37 | R |
|  | 7G | 1, 14D, 19 | R |
|  | 7T | 19, 66 | R |
| BW | 4N | 5, 27, 77 | R |
|  | 4P | 77 | R |
|  | 4T | 27 | R |
| DP | 5C | 24, HPVVS42L1* | R |
|  | 5D | 24, 38, 77 | R |
| RA | F | 5, 10, 27 | R |
| RW | 7B | 14D, 77, HPVVS92L1* | R |
|  | 7C | 14D | R |
|  | 7D | 10, 14D, 24 | R |
| LS | 7J | 38-rel | RP |
|  | 7K | 38-rel, HPVVS92L1* | RP |
|  | 7R | 38-rel | R |
| AB | 5J | 23, 77 | R |

Arg and Pro status p53 alleles in SCCs of renal transplant recipients. Note that unlike cervical tumors, different cutaneous lesions derived from the same patient, often contain more than one HPV type.
*indicates the locus name for an HPV sequence available in the GenBank database for which the full genome sequence has not yet been published (Accession Numbers are in parentheses):
HPVRTRx1 (L38918), HPV group24 B1
HPVRTRx5 (L38922), HPV group B1
HPVVS42L1 (X79943), HPV group B1
HPVVS92L1 (X79943), HPV group B1

These results again reveal a pronounced susceptibility to tumor associated with the p53arg allele with a striking excess of Arg (87.5%) relative to Arg/Pro (12.5%) and Pro (0%) alleles in these cutaneous HPV-containing tumors.

Since biopsies of tumors are invariably contaminated with either stromal tissue or inflammatory cells, we were interested to determine the effect of mixing either p53Arg or p53Pro DNA templates in a single reaction which would serve as a guide for the level of contaminating non-tumor cells. When the PCR reactions were performed using plasmid DNA containing either p53Arg or p53Pro sequences at a ratio of 95:5 or 5:95, using 100 ng of either DNA as the largest input, the product derived from the lower copy number allele was effectively amplified to the same degree as that from the higher input DNA under these conditions (FIG. 3b) indicating that amplification of one allele was not affected by the presence of the other.

Plasmid DNA known to encode either the Arg of Pro allele cloned a pcDNA vector, was PCR amplified either singly, or in the presence of the plasmid containing the other allele, using primers which specifically detect only one allele. The specific products of the Arg (141 bp) or Pro (277 bp) allele were detected only from the plasmid containing that allele, even in the presence of excess competitor template.

The location of the polymorphism at codon 72 and the positions of the primers used in the PCR study are indicated in FIG. 3a.

Distinguishing true heterozygote DNA samples from those tumor biopsies containing contaminating non-tumor tissue proved relatively straightforward, since amplification of genomic DNA from heterozygous individuals generated products which were routinely of about equal intensity, and never exceeded a two-fold difference as determined by quantitation of the radioactive products. To assess for possible stromal contamination genomic DNA samples known to be homozygous for either Pro or Arg alleles were mixed in the same ratios, using 100 ng total genomic DNA as the higher input. In this case we found that whichever DNA was in the lowest copy amplified to a far less degree than the higher copy DNA (FIG. 3c).

Mixing of templates was in FIG. 3b using 100 ng of total genomic DNA as the larger input.

In only two samples was contamination with non-tumor tissue detected as determined by the ratio of the PCR products, where the ratios of the intensities of the Arg/Pro products ranged between 1:20 to 1:40, which was very similar to the banding patterns generated by the deliberately mixed samples in FIG. 3c.

Based on this research, in the context of HPV-associated disease, individuals having only p53arg alleles can therefore be considered to be at a higher risk of developing malignancies than individuals retaining at least one copy of the p53pro allele. Considering that we can easily detect a 5% contamination of our samples with the other allele and that tumor biopsies are routinely contaminated with 10–50% of stromal tissue, the fact that the Pro allele was not detected in the vast majority of tumor biopsies suggests that the patients were homozygous for the Arg allele. Noteworthy also is that the codon 72 polymorphism is located in a recently identified SH3 domain which was required for efficient grown suppression by p53.

Taken together, these results demonstrate a significant susceptibility associated with the p53Arg allele to developing HPV-associated malignancies and furthermore suggest that the p53 polymorphic variants are not functionally equivalent as had been previously believed. These findings will have an immediate impact on screening programs as they suggest that the p53 genotype must now also be taken into consideration in the management of individuals with abnormal PAP smears and/or cervical neoplasia and individuals who are immunosuppressed. Such programs may have longer term implications for increased observation and perhaps earlier treatment of individuals with HPV infections and HPV-associated neoplasias.

The present invention will be more readily understood by referring to the following examples which are given to illustrate the invention rather than to limit its scope.

EXAMPLE I

The p53 genotype could be determined in individuals who are presented with an abnormal PAP smear. Individuals who's are determined to be homozygous for p53Arg alleles (p53Arg/p53Arg) would therefore be classified as at greater risk of developing HPV-associated cervical neoplasia and cervical cancer. The homozygous p53Arg individuals could then be treated by clinicians in a more aggressive manner than individuals who have at least on p53Pro allele.

EXAMPLE II

Considerable effort is under way to develop a vaccine against HPV to reduce the incidence of cervical neoplasia and cervical cancer. Individuals who's are determined to be homozygous for p53Arg alleles (p53Arg/p53Arg) would therefore be classified as at greater risk of developing HPV-associated cervical neoplasia and cervical cancer. The homozygous p53Arg individuals could then be preferentially vaccinated because they are at greatest risk for developing HPV-associated pathologies such as cancer.

EXAMPLE III

Individuals can become immunosuppressed for a variety of reasons such as caused by immunosuppressive drugs or infectious agents such as HIV. Immunosuppressed individuals who are determined to be homozygous for p53Arg alleles (p53Arg/p53Arg) would therefore be classified as at greater risk of developing HPV-associated pathologies such as cancer.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A screening method to identify individuals at risk of developing diseases associated with different polymorphic forms of wildtype p53; which comprises the steps of:
   a) obtaining a biological sample from an individual; and
   b) determining the presence of p53pro or p53arg wildtype alleles in said sample;
   wherein an allele pattern selected from the group consisting of p53pro/p53pro, p53arg/p53arg and p53pro/p53arg is indicative of a risk of developing diseases associated with different polymorphic forms of wildtype p53.

2. The screening method of claim 1, wherein said diseases are selected from the group consisting of neoplasia, cancers, viral infections, and immunosuppression.

3. The screening method of claim 2, wherein said diseases are caused by a virus.

4. The screening method of claim 3, wherein said virus is human papillomavirus.

5. The screening method of claim 4, wherein said disease is selected from the group consisting of cervical warts, cervical neoplasia, or cervical cancer.

6. The screening method of claim 4, wherein the patient allele pattern is p53arg/p53arg which is indicative of an individual at greater risk of developing said diseases.

7. The screening method of claim 1, wherein the determining step b) consists in at least one of:
   a) amplifying by polymerase chain reaction;
   b) sequencing DNA or protein;
   c) hybridizing with at least one probe specific to either p53pro or p53arg DNA; and
   d) immunodetecting with at least one antibody specific to either p53pro or p53arg protein to identify the p53pro or p53arg alleles.

8. The screening method of claim 1, wherein the patient is under immunosuppressing therapy and is more susceptible to viral infections and viral pathologies.

9. The screening method of claim 8, wherein the viral pathology is skin cancer associated with human papillomaviruses.

10. A screening method for potential vaccination candidates in any HPV vaccination program, which comprises the steps of:
    a.) obtaining a biological sample from a candidate; and
    b.) determining the presence of p53pro or p53arg wildtype alleles in said candidate;
    wherein said p53arg/p53arg patients should be preferentially vaccinated.

11. The screening method of claim 1, wherein said individuals have an abnormal PAP smear, cervical warts, or low grade cervical lesions.

12. The screening method of claim 1, wherein said individuals are newborns, or newborns to mothers with genital HPV infections.

* * * * *